United States Patent [19]

Fest et al.

[11] Patent Number: 4,859,235
[45] Date of Patent: Aug. 22, 1989

[54] PESTICIDAL α-METHYLSULPHONYL-BENZALDOXIMES AND CARBAMATES THEREOF

[75] Inventors: Christa Fest, Wuppertal; Gerd Hänssler, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 179,094

[22] Filed: Apr. 8, 1988

[30] Foreign Application Priority Data

Apr. 14, 1987 [DE] Fed. Rep. of Germany ....... 3712632

[51] Int. Cl.$^4$ ............................................. A01N 37/52
[52] U.S. Cl. ...................................... 71/103; 564/253; 564/255; 558/391
[58] Field of Search ................ 564/253, 255; 558/391; 74/103

[56] References Cited

U.S. PATENT DOCUMENTS

| 3,721,711 | 3/1973 | Maravety | 564/253 |
| 4,449,999 | 5/1984 | Sturm et al. | 71/103 |
| 4,497,745 | 2/1985 | Martin | 71/103 |
| 4,716,176 | 12/1987 | Fest et al. | 564/255 |

Primary Examiner—James H. Reamer
Attorney, Agent, or Firm—Sprung Horn Kramer & Woods

[57] ABSTRACT

Pesticidally active novel α-methylsulphonylbenzaldoxime and their carbamates of the formula

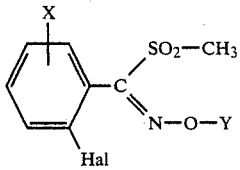

in which
Y represents H or —CO—NH—R,
R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl having 5 to 7 carbon atoms which is optionally monosubstituted to pentasubstituted by alkyl having 1 to 4 carbon atoms, or phenyl which is optionally monosubstituted to pentasubstituted by alkyl having 1 to 6 carbon atoms, alkoxy having 1 to 4 carbon atoms, halogenoalkyl or halogenoalkoxy in each case having 1 to 4 carbon atoms and 1 to 5 halogen atoms, and halogen, these substituents being identical or different,
Hal represents halogen, and
X represents hydrogen or halogen.

13 Claims, No Drawings

PESTICIDAL α-METHYLSULPHONYL-BENZALDOXIMES AND CARBAMATES THEREOF

The present invention relates to new α-methylsulphonyl-benzaldoxime carbamates, a process for their preparation, and their use for combating pests.

A number of benzaldoximes, such as, for example, α-phenylsulphonyl-2,6-dichloro-benzaldoxime, have already been disclosed, as has their use as plant-protection agents; above all, their use in agents for combating stinking smut of wheat has been disclosed (cf. Swiss Patent No. 423,350).

In addition, α-phenylsulphonyl-benzaldoxime carbamates and their use in plant protection have been disclosed (cf. DE-OS (German Published Specification) No. 3,520,943).

New α-methylsulphonyl-benzaldoxime carbamates of the general formula (I)

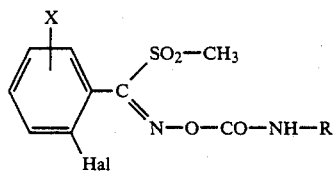

in which

R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl having 5 to 7 carbon atoms which is optionally monosubstituted to pentasubstituted by alkyl having 1 to 4 carbon atoms, or phenyl which is optionally monosubstituted to pentasubstituted by alkyl having 1 to 6 carbon atoms, alkoxy having 1 to 4 carbon atoms, halogenoalkyl or halogenoalkoxy in each case having 1 to 4 carbon atoms and 1 to 5 halogen atoms, and halogen, these substituents being identical or different, Hal represents halogen, such as fluorine, chlorine, bromine and iodine, and X represents hydrogen or halogen, such as fluorine, chlorine, bromine and iodine, have been found.

It has furthermore been found that the α-methylsulphonyl-benzaldoxime carbamates of the general formula (I)

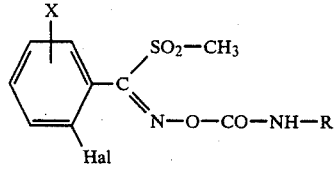

R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl having 5 to 7 carbon atoms which is optionally monosubstituted to pentasubstituted by alkyl having 1 to 4 carbon atoms, or phenyl which is optionally monosubstituted to pentasubstituted by alkyl having 1 to 6 carbon atoms, alkoxy having 1 to 4 carbon atoms, halogenoalkyl or halogenoalkoxy in each case having 1 to 4 carbon atoms and 1 to 5 halogen atoms, and halogen, these substituents being identical or different, Hal represents halogen, and X represents hydrogen or halogen, are obtained when α-methylsulphonyl-benzaldoximes of the general formula (II)

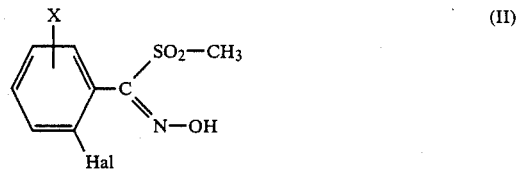

are reacted with isocyanates of the formula (III) in which

R, Hal and X have the abovementioned meanings, if appropriate in the presence of solvents or diluents at temperatures from 0° C. to 100° C.

The α-methylsulphonylbenzaldoxime carbamates of the general formula (I) according to the invention have strong biological properties, above all fungicidal properties.

Surprisingly, the compounds according to the invention at the same time exhibit a considerably greater activity, above all a fungicidal activity, than the compounds known from the prior art which are very similar compounds structurally and regarding their action.

The compounds of the formula (I) according to the invention can be produced as syn or anti isomers or as mixtures thereof in various ratios. The invention relates both to the pure isomer and to the isomeric mixtures.

Formula (I) provides a general definition of the α-methylsulphonyl-benzaldoxime carbamates according to the invention. Preferred compounds of the formula (I) are those in which R represents straight-chain or branched alkyl having 1 to 4 carbon atoms, such as methyl, ethyl, n-propyl, iso-propyl, n-butyl, iso-butyl, sec.-butyl and tert.-butyl, halogenoalkyl having 1 to 6 carbon atoms and 1 to 3 identical or different halogen atoms, such as fluorine, chlorine, bromine and iodine, for example 2-chloroethyl, 3-chloro-n-propyl, 4-chloro-n-butyl, 4-chloro-n-pentyl and 6-chloro-n-hexyl, cyanoalkyl having 1 to 5 carbon atoms, for example 3- or 5-cyano-n-pentyl, tosyl, benzyl, cycloalkyl having 6 or 7 carbon atoms which is optionally monosubstituted, disubstituted or trisubstituted by identical or different alkyl having 1 to 3 carbon atoms, such as methyl, ethyl, n-propyl and iso-propyl, or phenyl which is optionally monosubstituted, disubstituted or trisubstituted by alkyl having 1 to 4 carbon atoms, such as, for example, methyl, ethyl, n-propyl, iso-propyl, n-butyl, iso-butyl, sec.-butyl and tert.-butyl, by alkoxy having 1 to 3 carbon atoms, such as methoxy, ethoxy, n-propoxy and iso-propoxy, by halogenoalkyl or halogenoalkoxy in each case having 1 to 3 carbon atoms and 1 to 3 identical or different halogen atoms, such as fluorine, chlorine, bromine and iodine, such as, for example, trifluoromethyl, trichloromethyl, dichlorofluoromethyl, 2-chloroethyl, 2-fluoroethyl, trifluoromethoxy, dichlorofluoromethoxy, 2-chloroethoxy and 2-fluoroethoxy, and by halogen, such as fluorine, chlorine, bromine and iodine, these substituents being identical or different, Hal represents fluorine or chlorine, and X represents hydrogen, fluorine or chlorine.

Particularly preferred compounds of the formula (I) are those in which

R represents methyl, ethyl, n-propyl, iso-propyl, n-butyl, iso-butyl, tert.-butyl, 6-chloro-n-hexyl, 5-cyano-n-pentyl, tosyl, benzyl, cyclohexyl which is monosubstituted, disubstituted or trisubstituted by methyl or ethyl, or phenyl which is monosubstituted, disubstituted or trisubstituted by methyl, ethyl, n-propyl, iso-propyl, methoxy, ethoxy, trifluoromethoxy, chlorine and fluorine, these substituents being identical or different, Hal represents fluorine or chlorine, and X represents hydrogen, fluorine or chlorine.

In particular, compounds of the formula (I) which may be mentioned are those in which R represents methyl, ethyl, n-propyl, iso-propyl, n-butyl, iso-butyl, tert.-butyl, 6-chloro-n-hexyl, 5-cyano-n-pentyl, benzyl, tosyl, 3,5,5-trimethylcyclohexyl, cyclohexyl, 4-methyl-cyclohexyl, 4-trifluoromethoxyphenyl, 2-, 3- or 4-methyl-phenyl, 3-chloro-4-methyl-phenyl, 3-methyl-4-chlorophenyl, 3- or 4-chlorophenyl, 3,4- or 3,5-dichloro-phenyl, 3-trifluoromethyl-phenyl, 4-ethoxy-phenyl, 3-chloro-4-trifluoromethylphenyl, 2,6-dimethylphenyl or 3,6-di-isopropyl-phenyl, Hal represents fluorine or chlorine, and X represents fluorine or chlorine.

Very particularly preferred are the compounds of the formula (I) in which

R represents methyl, ethyl, tosyl, 4-trifluoromethoxyphenyl or 3,5,5-trimethyl-cyclohexyl, and Hal and X have the abovementioned meanings.

Alkyl, halogenoalkyl, alkoxy, halogenoalkoxy and cyanoalkyl may in each case be straight-chain or branched in the alkyl part where they are also mentioned.

If α-methylsulphonyl-2,6-dichlorobenzaldoxime and methyl isocyanate are used as starting materials, the course of the reaction of the process according to the invention may be represented by the following equation:

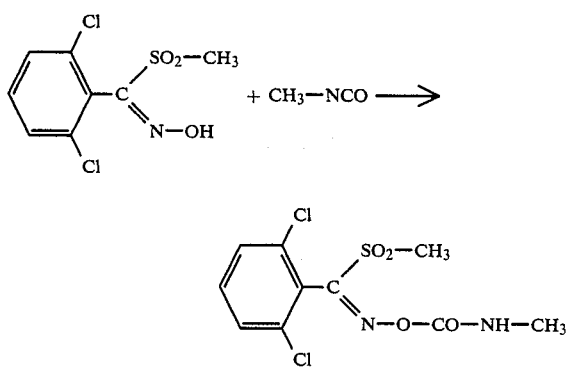

Formula (II) defines the α-methylsulphonyl-benzaldoximes required as starting materials for carrying out the process according to the invention. These compounds are new and part of this invention. They can be prepared by processes which are known in principle (cf., for example, Swiss No. 423,350 or Tetrahedron 1975, 31 (6), 597–600), by reacting α-halogeno-benzaldoximes of the general formula (IV)

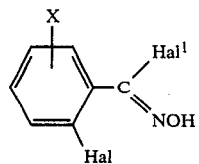

in which

HaL$^1$ represents halogen, preferably chlorine, and

X and Hal have the abovementioned meanings, with methanesulphinic acids of the general formula (V)

$$CH_3-SO_2M \qquad (V)$$

in which

M represents hydrogen or an alkali metal equivalent, if appropriate in the presence of a solvent and if appropriate in the presence of an acid-binding agent, at temperatures between 0° C. and 60° C.

The compounds of the formula (II) are also not only interesting compounds for highly active final products, but also exhibit a good biological action themselves.

The process for the preparation of the starting compounds of the formula (II) can be carried out, if desired, in the presence of a solvent or diluent. Suitable as such are preferably alcohols, such as methanol.

The reaction temperatures may be varied within a relatively wide range. In general, the process is carried out between 0° and 60° C., preferably between 15° and 30° C.

The α-halogenobenzaldoximes of the general formula (IV) can be obtained in a known fashion by halogenating the appropriate benzaldoximes (cf., for example, CH No. 423,350 Example I).

The alkanesulphinic acids of the formula (V) are long-known basic chemicals.

Formula (III) provides a general definition of the isocyanates which are furthermore required as starting materials. These are known compounds of organic chemistry.

The process according to the invention for the preparation of the compounds of the formula (I) can be carried out, if desired, in the presence of a solvent or diluent. Suitable as such are, in principle, all inert organic solvents. Hydrocarbons, optionally chlorinated, such as, for example, benzene, toluene, xylene, methylene chloride, chloroform, carbon tetrachloride, chlorobenzene and dichlorobenzene, are preferably used.

The reaction temperatures may be varied within a relatively wide range. In general, the process is carried out between 0° and 100° C., preferably between 15° and 50° C.

When carrying out the process according to the invention, the reactants are allowed to react with one another in approximately equimolar ratios. Since the reaction is sometimes exothermic, cooling is recommended. The reaction mixture is worked up in a conventional fashion, especially by filtering the precipitated reaction product off under suction, washing and drying.

In order to complete the reaction, a few drops of a base, such as, for example, triethylamine, can be added if necessary.

The active compounds according to the invention have a strong biological action and can be employed in practice for combating undesired pests. The active compounds are suitable for use as pesticides, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: *Xanthomonas* species, such as, for example, *Xanthomonas campestris* pv. oryzae; *Pseudomonas* species, such as, for example, *Pseudomonas syringae* pv. *Lachrymans*; *Erwinia* species, such as, for example, *Erwinia amylovora*; *Pythium* species, such as, for example, *Pythium ultimum*; *Phytophthora* species, such as, for example, *Phytophthora infestans*; *Pseudoperonospora* species, such as, for example, *Pseudoperonospora humuli* or *Pseudoperonospora cubensis*; *Plasmopara* species, such as, for example, *Plasmopara viticola*; *Peronospora* species, such as, for example, *Peronospora pisi* or *P. brassicae*; *Erysiphe* species, such as, for example, *Erysiphe graminis*; *Sphaerotheca* species, such as, for example, *Sphaerotheca fuliginea*; *Podosphaera* species, such as, for example, *Podosphaera leucotricha*; *Venturia* species, such as, for example, *Venturia inaequalis*; *Pyrenophora* species, such as, for example, *Pyrenophora teres* or *P. gramines* (conidia form: *Drechslera*, syn: *Helminthosporium*); *Cochliobolus* species, such as, for example, *Cochliobolus sativus* (conidia form: *Drechslera*, syn: *Helminthosporium*); *Uromyces* species, such as, for example, *Uromyces appendiculatus*; *Puccinia* species, such as, for example, *Puccinia recondita*; *Tilletia* species, such as, for example, *Tilletia caries*; *Ustilago* species, such as, for example, *Ustilago nuda* or *Ustilago avenae*; *Pellicularia* species, such as, for example, *Pellicularia sasakii*; *Pyricularia* species, such as, for example, *Pyricularia oryzae*; *Fusarium* species, such as, for example, *Fusarium culmorum*; *Botrytis* species, such as, for example, *Botrytis cinerea*; *Septoria* species, such as, for example, *Septoria nodorum*; *Leptosphaeria* species, such as, for example, *Leptosphaeria nodorum*; *Cercospora* species, such as, for example, *Cercospora canescens*; *Alternaria* species, such as, for example, *Alternaria brassicae* and *Pseudocercosporella* species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be used particularly successfully for combating fruit diseases, caused, for example, by *Venturia* species, or rice diseases, caused, for example, by *Pyricularia* species. The good Oomycetes action and the bactericidal in vitro action are also worth mentioning.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action. The compounds of the formula (I) according to the invention exhibit a particularly good action against pathogens of fruit diseases, caused, for example, by Venturia species, and rice diseases, caused by Pyricularia species. Furthermore, the good Oomycetes action and the in vitro action against bacteria may be mentioned.

In appropriate concentrations, the substances according to the invention also exhibit herbidal actions.

USE EXAMPLES

In the following use examples, the compounds shown below are used as comparison substances:

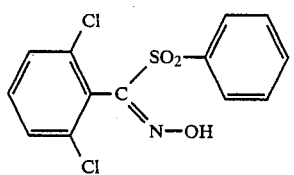

α-phenylsulphonyl-2,6-dichlorobenzaldoxime (known from Swiss No. 423,350),

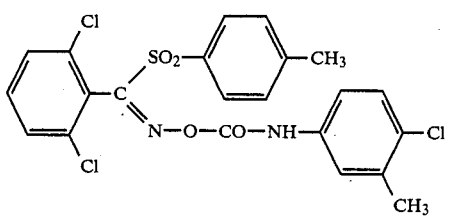

α-(4-methylphenylsulphonyl)-2,6-dichlorobenzaldoxime (4-chloro-3-methylphenyl)-carbamate,

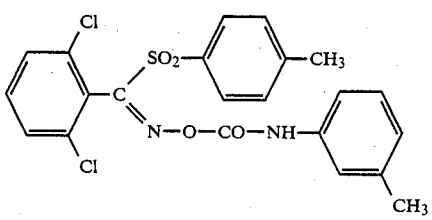

α-(4-methylphenylsulphonyl)-2,6-dichlorobenzaldoxime (3-methylphenyl)-carbamate,

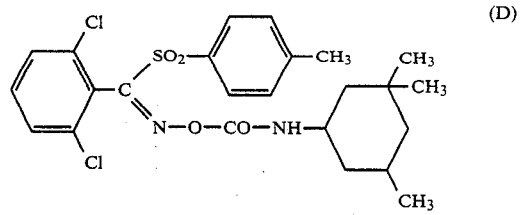

α-(4-methylphenylsulfonyl)-2,6-dichlorobenzaldoxime (3,3,5-trimethylcyclohexyl)-carbamate, and

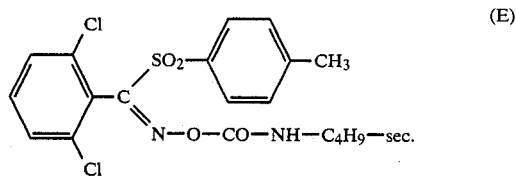

α-(4-methylphenylsulfonyl)-2,6-dichlorobenzaldoxime sec.-butyl-carbamate (B-E known from DE-OS (German Published Specification No. 3,520,943).

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compounds according to preparation Examples 6, 3, 1, 1A, 2A and 3A exhibit a clearly superior activity compared to the prior art.

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmsspheric humidity for 1 day.

The plants are then placed in a greenhouse at 20° C. and a relative atmospheric humidity of about 70%.

Evaluation is carried out 12 days after the inoculation.

In this test, for example, the compounds according to preparation Examples 1, 2, 6, 1A and 3A exhibit a clearly superior activity compared to the prior art.

PREPARATION EXAMPLES

Example 1:

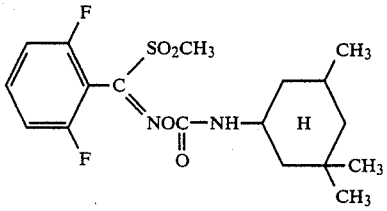

10 g (0.043 mol) of α-methylsulphonyl-2,6-difluorobenzaldoxime are suspended in 150 ml of methylene chloride, and 7.2 g (0.043 mol) of 3,3,5-trimethylcyclohexyl isocyanate are added, a few drops of triethylamine being added. The reaction mixture is kept at room temperature overnight, and a clear solution is produced. This solution is filtered to remove some impurities, and subsequently evaporated in vacuo. The amorphous residue is recrystallized from isopropanol. 9.1 g (55% of theory) of α-methyl- sulphonyl-2,6-difluorobenzaldoxime 3,3,5-trimethylcyclohexyl carbamate of melting point 152° C. are obtained.

The compounds of the formula (I)

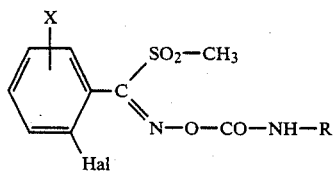

are prepared analogously to Example 1 and/or the general instructions:

| Example No. | X 2-position | Hal | R | Melting point [°C.] |
|---|---|---|---|---|
| 2 | Cl | Cl | $C_2H_5$ | 184 |
| 3 | F | F | $C_2H_5$ | 116 |
| 4 | Cl | Cl | ![m-CF3-phenyl] | 173 |
| 5 | Cl | Cl | ![3,3,5-trimethylcyclohexyl] | 168 |
| 6 | Cl | Cl | $-(CH_2)_6-Cl$ | 90 |
| 7 | Cl | Cl | ![2-methylphenyl] | |
| 8 | Cl | Cl | $CH_3$ | 158 |
| 9 | Cl | Cl | $C_3H_7-n$ | 168 (decomp.) |
| 10 | Cl | Cl | $C_3H_7-i$ | 150 (decomp.) |
| 11 | Cl | Cl | $C_4H_9-n$ | 96 |
| 12 | Cl | Cl | $C_4H_9-i$ | 123 |
| 13 | Cl | Cl | $C_4H_9-sec.$ | 122 |
| 14 | Cl | Cl | ![3-methylphenyl] | 118 |
| 15 | Cl | Cl | ![4-methylphenyl] | 162 (decomp.) |
| 16 | Cl | Cl | ![4-ethoxyphenyl] | 160 (decomp.) |
| 17 | Cl | Cl | ![cyclohexyl] | 167 |
| 18 | Cl | Cl | ![3-chloro-4-methylphenyl] | 152 (decomp.) |

PREPARATION OF THE STARTING COMPOUNDS

Example 1 A:

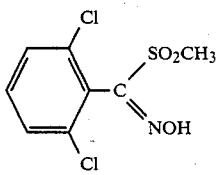

45 g (0.2 mol) of α-chloro-2,6-dichlorobenzaldoxime are dissolved in 200 ml of methanol, and 22.5 g (0.2 mol) of sodium S-methyl sulphite are added. The reaction proceeds exothermically. The reaction mixture is stirred overnight at room temperature. It is subsequently poured into about 1 liter of ice water and extracted by stirring, and the product is filtered off under suction, washed and ried. After recrystallization from isopropanol, 35.5 g 66% of theory) of α-methylsulphonyl-2,6-dichlorobenzaldoxime of melting point 193° C. are obtained.

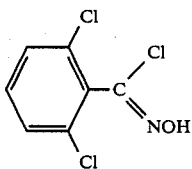

95 g (0.5 mol) of 2,6-dichlorobenzaldoxime are suspended in 1000 ccm of carbon tetrachloride. 36 g of chlorine are passed into this suspension. The temperature remains below 15? C. The oxime must dissolve. Immediately thereafter, the solution is evaporated in vacuo. The majority of the residue crystallizes out. It is recrystallized from hot cyclohexane. 50 g (45% of theory) of α-chlora-2,6-dichlorobenzaldoxime of melting point 114 C. are obtained.

The compounds of the formula (II)

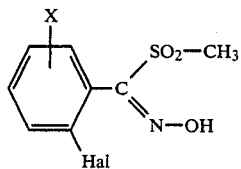

(II)

are prepared analogously to Example 1A or the general instructions:

| Example No. | X 2-position | Hal | Melting point [°C.] |
|---|---|---|---|
| 2A | H | Cl | 161 |
| 3A | F | F | 153 |
| 4A | Cl | F | 168 |

It will be understood that the specification and examples are illustrative but not limitative of the present invention and that other embodiments within the spirit and scope of the invention will suggest themselves to those skilled in the art.

We claim:

1. A compound of the formula

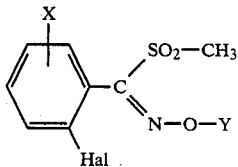

in which

Y represents H or —CO—NH—R,

R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl having 5 to 7 carbon atoms which is optionally monosubstituted to pentasubstituted by alkyl having 1 to 4 carbon atoms, or phenyl which is optionally monosubstituted to pentasubstituted by alkyl having 1 to 6 carbon atoms, alkoxy having 1 to 4 carbon atoms, halogenoalkyl or halogenoalkoxy in each case having 1 to 4 carbon atoms and 1 to 5 halogen atoms, and halogen, these substituents being identical or different, Hal represents halogen, and X represents hydrogen or halogen.

2. A compound according to claim 1, in which

R represents straight-chain or branched alkyl having 1 to 4 carbon atoms, halogenoalkyl having 1 to 6 carbon atoms and 1 to 3 identical or different halogen atoms, cyanoalkyl having 1 to 5 carbon atoms in the alkyl part, tosyl, benzyl, cycloalkyl having 6 or 7 carbon atoms which is optionally monosubstituted, disubstituted or trisubstituted by identical or different, straight-chain or branched alkyl having 1 to 3 carbon atoms, or phenyl which is optionally monosubstituted, disubstituted or trisubstituted by straight-chain or branched alkyl having 1 to 4 carbon atoms, straightchain or branched alkoxy having 1 to 3 carbon atoms, halogenoalkyl or halogenoalkoxy in each case having 1 to 3 carbon atoms and 1 to 3 halogen atoms, and halogen, these substituents being identical or different, Hal represents fluorine or chlorine, and X represents hydrogen, fluorine or chlorine.

3. A compound according to claim 1, in which

R represents methyl, ethyl, n-propyl, iso-propyl, n-butyl, iso-butyl, tert.-butyl, 6-chloro-n-hexyl, 5-cyano-n-pentyl, tosyl, benzyl, cyclohexyl, cyclohexyl which is monosubstituted, disubstituted or trisubstituted by methyl or ethyl, or phenyl which is monosubstituted, disubstituted or trisubstituted by methyl, ethyl, n-propyl, iso-propyl, methoxy, ethoxy, trifluoromethoxy, chlorine and fluorine, the substituents being identical or different, Hal represents fluorine or chlorine, and X represents hydrogen, fluorine or chlorine.

4. A compound according to claim 1, in which

R represents methyl, ethyl, n-propyl, iso-propyl, n-butyl, iso-butyl, tert.-butyl, 6-chloro-n-hexyl, 5-cyano-n-pentyl, benzyl, tosyl, cyclohexyl, 3,5,5-trimethyl-cyclohexyl, 4-methyl-cyclohexyl, 4-trifluoromethoxy-phenyl, 2-, 3- or 4-methyl-phenyl, 3-chloro-4-methylphenyl, 3-methyl-4-chlorophenyl, 3- or 4-chlorophenyl, 3,4- or 3,5-dichloro-phenyl, 3-trifluoromethyl-phenyl, 4-ethoxy-phenyl, 3-chloro-4-trifluoromethylphenyl, 2,6-dimethyl-phenyl or 3,6-di-isopropyl-phenyl, Hal represents fluorine or chlorine.

5. A compound according to claim 1, in which Y is H.

6. A compound according to claim 1, in which Y is —CO—NH—R.

7. A compound according to claim 1, wherein such compound is α-methyl-sulphonyl-2,6-difluorobenzaldoxime 3,3,5-trimethylcyclohexyl carbamate of the formula

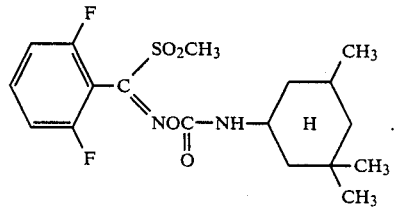

8. A compound according to claim 1, wherein such compound is α-methylsulphonyl-2,6-dichlorobenzaldoxime ethyl carbamate of the formula

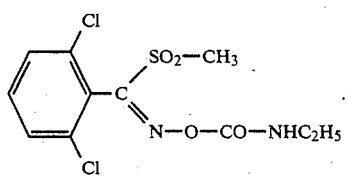

9. A compound according to claim 1, wherein such compound is α-methylsulphonyl-2,6-dichlorobenzaldoxime n-chlorohexyl carbamate of the formula

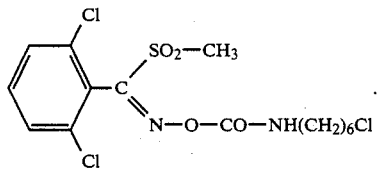

10. A compound according to claim 1, wherein such compound is α-methylsulphonyl-2,6-difluorobenzaldoxime of the formula

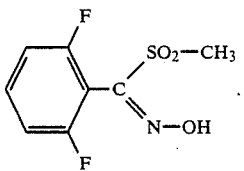

11. A pesticidal composition comprising a pesticidally effective amount of a compound according to claim 1 and a diluent.

12. A method of combating pests which comprises applying to such pests or to a pest habitat a pesticidally effective amount of a compound according to claim 1.

13. The method according to claim 12, wherein such compound is
- α-methyl-sulphonyl-2,6-difluorobenzaldoxime 3,3,5-trimethylcyclohexyl carbamate,
- α-methylsulphonyl-2,6-dichlorobenzaldoxime ethyl carbamate,
- α-methylsulphonyl-2,6-dichlorobenzaldoxime n-chlorohexyl carbamate or
- α-methylsulphonyl-2,6-difluorobenzaldoxime.

* * * * *